(12) United States Patent
Okajima

(10) Patent No.: US 6,890,776 B2
(45) Date of Patent: May 10, 2005

(54) SILICON OXIDE FILM EVALUATION METHOD AND SEMICONDUCTOR DEVICE FABRICATION METHOD

(75) Inventor: Takehiko Okajima, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 60 days.

(21) Appl. No.: 10/446,928

(22) Filed: May 29, 2003

(65) Prior Publication Data

US 2004/0082084 A1 Apr. 29, 2004

(30) Foreign Application Priority Data

Oct. 24, 2002 (JP) ........................................ 2002-309402

(51) Int. Cl.⁷ .............................................. H01L 21/66
(52) U.S. Cl. .......................... 438/16; 438/14; 438/778; 438/779; 438/787
(58) Field of Search ........................... 438/14, 16, 778, 438/779, 787

(56) References Cited

U.S. PATENT DOCUMENTS

| | | | | |
|---|---|---|---|---|
| 4,851,370 A | * | 7/1989 | Doklan et al. | 438/762 |
| 5,595,916 A | * | 1/1997 | Fujimura et al. | 438/16 |
| 5,660,895 A | * | 8/1997 | Lee et al. | 427/579 |
| 6,613,677 B1 | * | 9/2003 | Herbots et al. | 438/694 |
| 6,744,501 B2 | * | 6/2004 | Klose | 356/301 |
| 2002/0119607 A1 | * | 8/2002 | Miyasaka et al. | 438/151 |

FOREIGN PATENT DOCUMENTS

| | | |
|---|---|---|
| JP | 02-205047 | 8/1990 |
| JP | 07-221150 | 8/1995 |

OTHER PUBLICATIONS

Lucovsky et al., Low–temperature growth of silicon dioxide films: A study of chemical bonding by ellipsometry and infrared spectroscopy, *J. Vac. Sci. Technol. B*, 5 (Mar./Apr. 1987) 530.*

(Continued)

*Primary Examiner*—Christian Wilson
(74) *Attorney, Agent, or Firm*—Rabin & Berdo, P.C.

(57) ABSTRACT

A silicon oxide film formed on a compound semiconductor substrate is evaluated by estimating the quantity of silicon-silicon bonds operating as electron traps in the silicon oxide film from a peak with a wave number of 880/centimeter in the Fourier-transform infrared spectrum of the silicon oxide film. This peak, which is an indicator of silicon-silicon stretching vibration, provides an index of expected power performance degradation during operation of field-effect transistors incorporating the silicon oxide film as an interlayer. Power degradation can be reduced by fabricating the semiconductor device under conditions that reduce the estimated quantity of silicon-silicon bonds, without the need to measure the power degradation.

11 Claims, 8 Drawing Sheets

OTHER PUBLICATIONS

Trchova et al., Photoelectron and infrared spectroscopy of semi–insulating silicon layers, *J. Appl. Phys.*, 82 (Oct. 1997) 3519.*

Chen et al., Evidence for energy coupling from the Si–D vibration mode to the Si–Si and Si–O vibration modes at the $SiO_2$/Si interface, *Appl. Phys. Lett.*, 83 (Sep. 2003) 2151.*

Power et al., Refractive index at infrared wavelengths and dielectric permittivity of pure and fluorinated silicon dioxide from measurements of their thin films deposited on Si, *J. Phys. D: Appl. Phys.*, 37 (2004) 1362.*

James C.M. Hwang, "Relationship between gate lag, power drift, and power slump of pseudomorphic high electron mobility transistors", Solid–State Electronics 43 (1999), pp. 1325–1331.

"Si rings, Si clusters, and Si nanocrystals—different states of ultrathin $SiO_x$ layers", L. X. Yi et al.: Applied Physics Letters, vol. 81, No. 22; Max–Planck–Institute of Microstructure Physics, Weinberg 2, 06120 Halle, Germany; Nov. 25, 2002; pp. 4248–4250.

* cited by examiner

| | SiOx FILM AREA RATIO | Po (dB) | $\Delta P$ (dB) |
|---|---|---|---|
| SAMPLE 1 | 0.099 | 28.16 | −0.11 |
| SAMPLE 2 | 0.141 | 28.18 | −0.33 |
| SAMPLE 3 | 0.183 | 28.14 | −0.55 |

|  | ACTIVATION ENERGY (kcal/mol) |
|---|---|
| SILICON OXIDE FILM HAVING Si–Si BONDS | 5.88 |
| SILICON OXIDE FILM HAVING Si–H BONDS | 13.14 |

SILICON OXIDE FILM EVALUATION METHOD AND SEMICONDUCTOR DEVICE FABRICATION METHOD

BACKGROUND OF THE INVENTION

1. Field of the Invention

The present invention relates to a method of fabricating a semiconductor device in which a field-effect transistor (FET) having a silicon oxide interlayer film is formed on a compound semiconductor substrate, and more particularly to a method of evaluating the interlayer film in order to control the degradation of FET power characteristics due to electron trapping.

2. Description of the Related Art

When a high-output compound semiconductor FET is driven for an extended period of time, its power output degrades due to the effect of electrons trapped in the interlayer film, or between the compound semiconductor substrate and the interlayer film. A description of this effect is given in "Relationship between gate lag, power drift, and power slump of pseudomorphic high electron mobility transistors," Solid-State Electronics 43 (1999), pp. 1325–1331 (hereinafter, Reference 1).

One method of assessing the degradation of the interlayer film employs Fourier-transform infrared (FT-IR) spectroscopy, as described in Japanese Unexamined Patent Application Publication No. 7-221150 (hereinafter, Reference 2). In this method, the change in the FT-IR spectrum of an interlayer oxide film before and after operation of the FET is measured, and the degradation of the interlayer film is determined from the change.

Reference 1 deals with mitigation of the degradation of power characteristics of a high-output compound semiconductor FET having a silicon nitride film, but does not address the degradation of power characteristics of a high-output FET having a silicon oxide film formed on a compound semiconductor substrate.

Since the method described in Reference 2 requires measured data to be obtained after operation of the FET, degradation evaluation takes time. This method is not suitable for use during mass production of semiconductor devices.

It would be desirable to have a more practical method of controlling the degradation of power characteristics of high-output compound semiconductor FETs having a silicon oxide interlayer film.

SUMMARY OF THE INVENTION

An object of the present invention is to provide a simple and quick method of evaluating and controlling the degradation of power characteristics of a FET having a silicon oxide interlayer film during the film fabrication process.

The invention provides a method of evaluating a silicon oxide film formed on a compound semiconductor substrate. The method includes obtaining an FT-IR spectrum of the silicon oxide film, and estimating the quantity of silicon-silicon bonds operating as electron traps in the silicon oxide film from a peak with a wave number of 880/centimeter (880 $cm^{-1}$) in the FT-IR spectrum, this peak being an indicator of silicon-silicon stretching vibration.

The quantity of silicon-silicon bonds may be estimated directly from the area of the 880 $cm^{-1}$ peak, or by comparing this area with the area of another peak in the FT-IR spectrum, the other peak indicating silicon-oxygen stretching vibration.

The invention also provides a method of fabricating a semiconductor device including a FET having a silicon oxide interlayer film formed on a compound semiconductor substrate. The method includes analyzing the silicon oxide interlayer film by FT-IR spectroscopy and estimating the quantity of silicon-silicon bonds as described above, determining a fabrication process condition for forming the silicon oxide film so as to reduce the quantity of silicon-silicon bonds, and forming the interlayer silicon oxide film according to this fabrication process condition. The estimated quantity of silicon-silicon bonds provides an index of expected power performance degradation during operation of the FET, so fabricating the semiconductor device under a condition that reduces the estimated quantity of silicon-silicon bonds reduces the expected power degradation, without the need for actual measurement of the power degradation.

In an alternative method of fabricating a semiconductor device the estimated quantity of silicon-silicon bonds operating as electron traps in the interlayer film is used as an index of expected power performance degradation during operation of the FET. For example, the fabricated semiconductor devices can be graded according to the estimated quantity of silicon-silicon bonds.

DETAILED DESCRIPTION OF THE INVENTION

Figure 1:
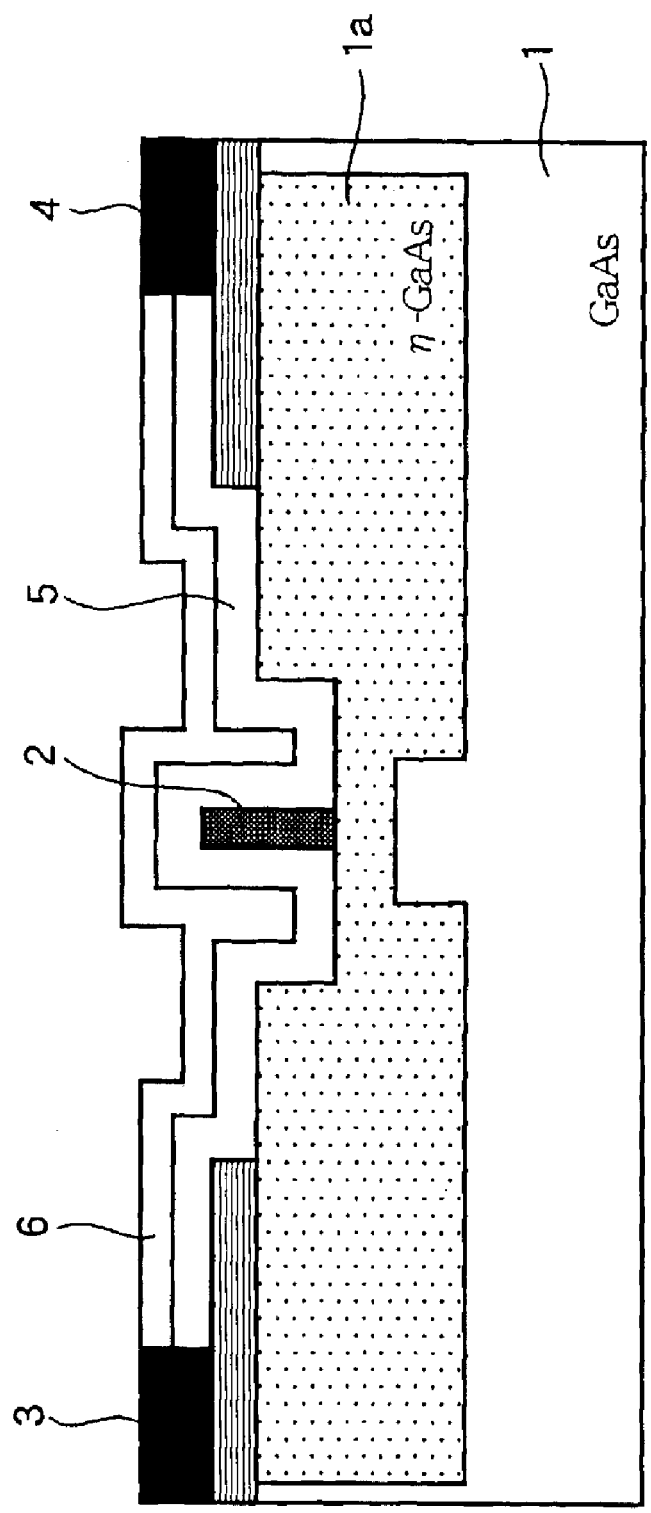
FIG. 1 is a sectional view of a high-output FET having a silicon oxide interlayer film formed on a compound semiconductor substrate.

Embodiments of the invention will now be described with reference to the attached drawings, in which like elements are indicated by like reference characters.

A sectional view of a high-output FET having a silicon substrate is shown in FIG. 1. The substrate is a gallium-arsenide (GaAs) substrate 1 with an n-type GaAs layer 1a, on which a gate electrode 2, a source electrode 3, a drain electrode 4, a silicon oxide film 5 (the interlayer film), and a silicon nitride film 6 (another interlayer film) are formed.

Figure 2:
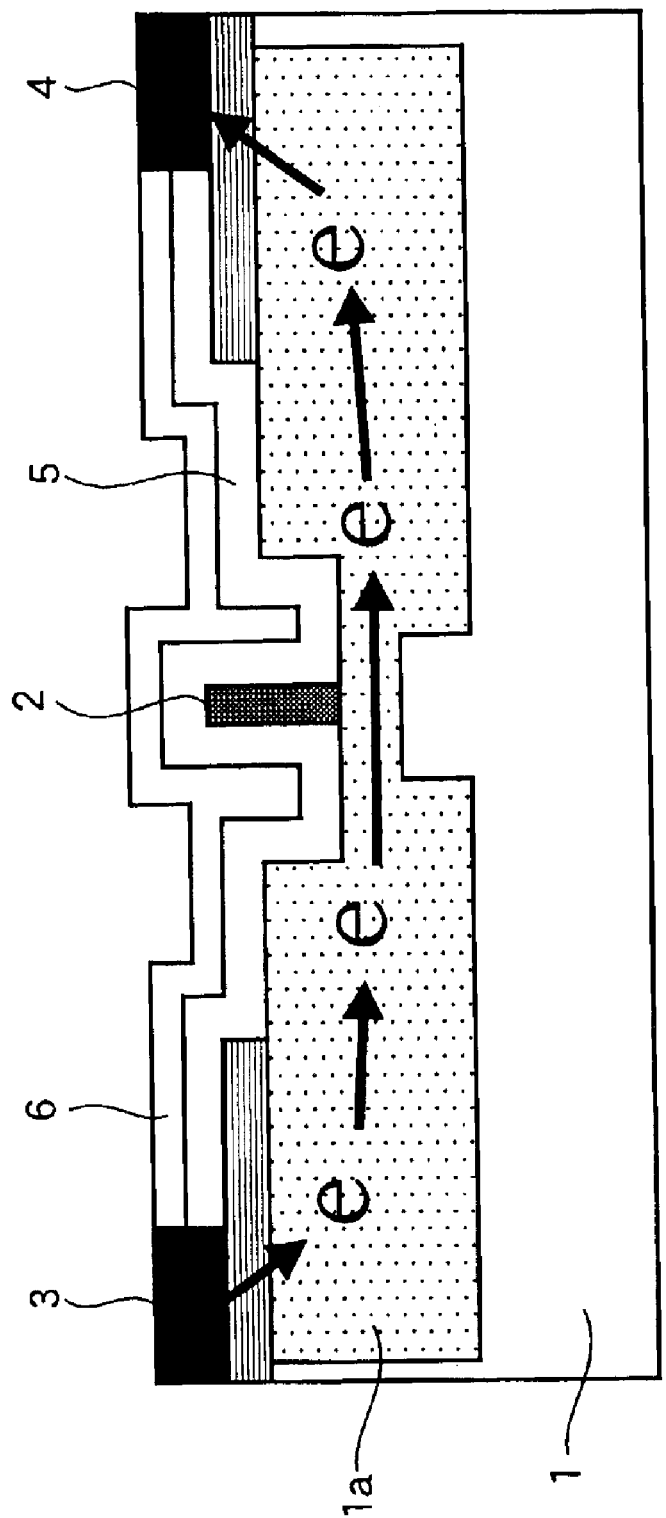
FIG. 2 schematically illustrates the operation of the high-output FET in FIG. 1.
Figure 3:
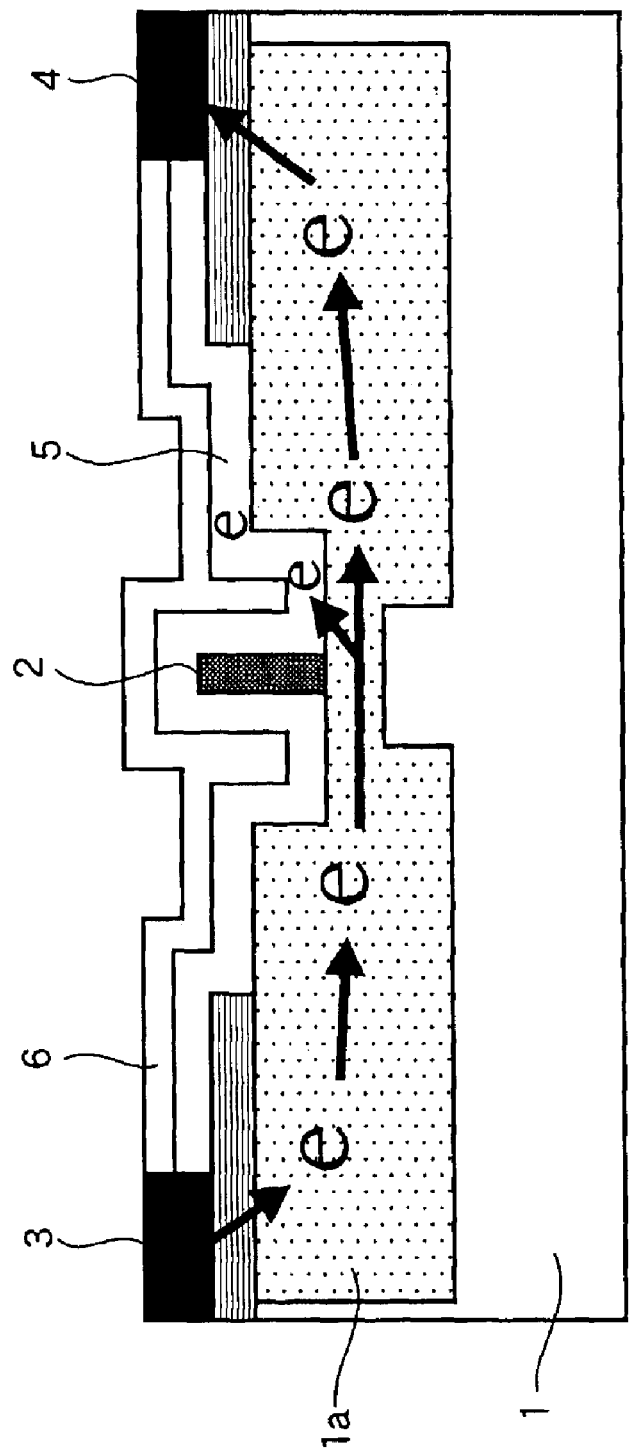
FIG. 3 schematically illustrates the electron hot-carrier effect during the operation of the high-output FET in FIG. 1.

FIG. 2 schematically illustrates the operation of the high-output FET. FIG. 3 schematically illustrates the electron hot-carrier effect during the operation of the high-output FET.

As shown in FIG. 2, electrons (e) injected from the source electrode 3 traverse the n-type GaAs layer 1a to reach the drain electrode 4. As shown in FIG. 3, some of the electrons become highly energetic or 'hot' carriers that are injected into the silicon oxide film 5. If the injected charges are trapped in the silicon oxide film 5, the power output characteristic of the FET is degraded.

Figure 4:
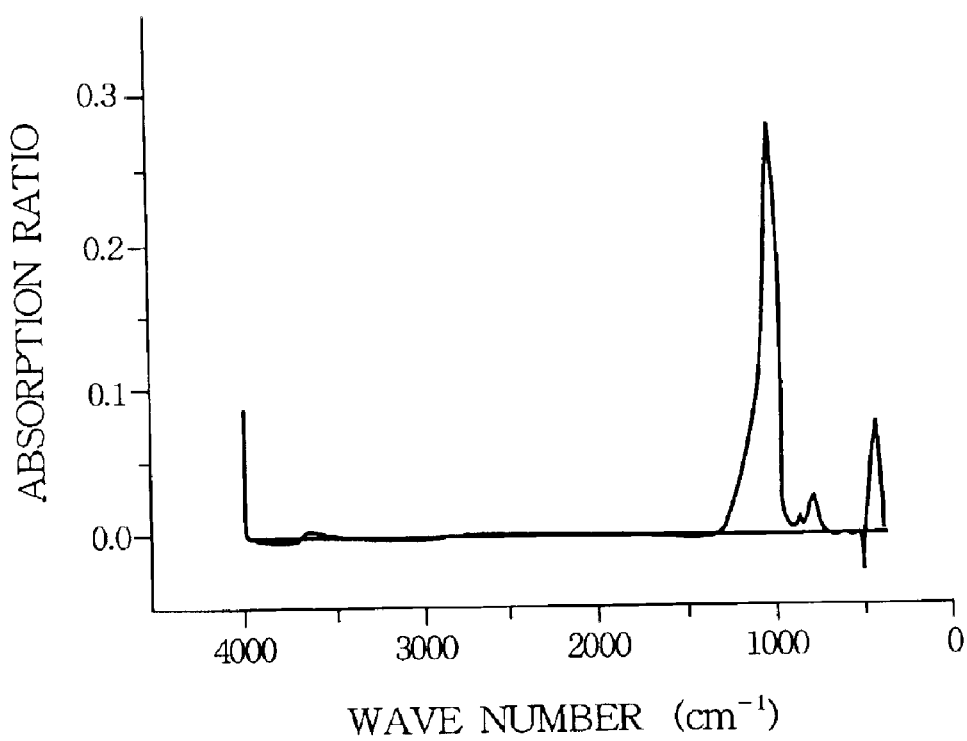
FIG. 4 shows an FT-IR spectrum obtained from a silicon oxide film deposited on a gallium-arsenide (GaAs) wafer substrate by low-pressure chemical vapor deposition (CVD)
Figures 5, 6:
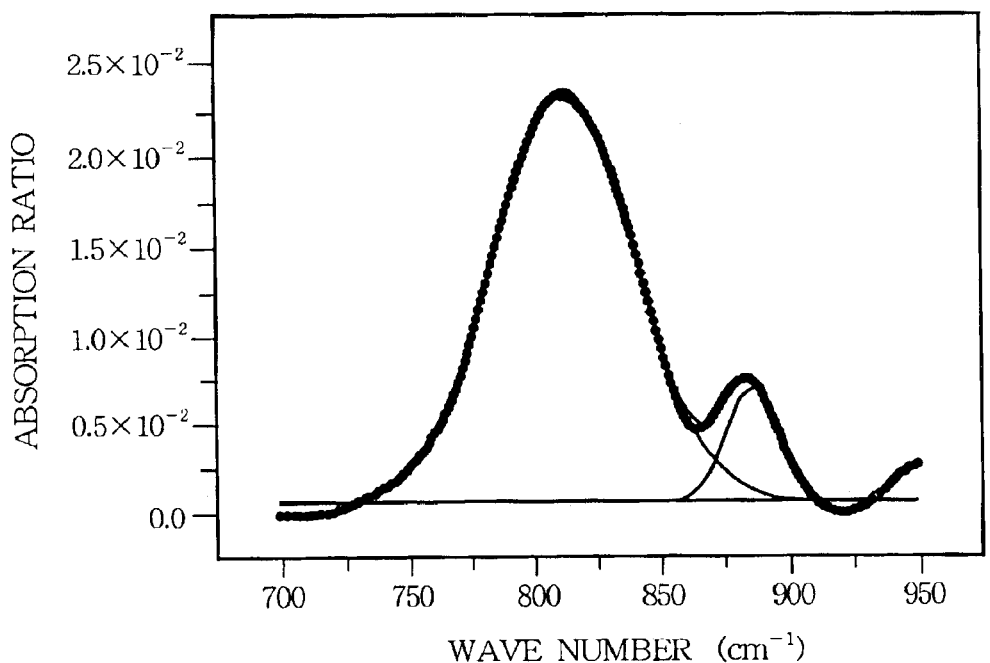
FIG. 5 shows an enlargement of the FT-IR spectrum in FIG. 4 between 700 $cm^{-1}$ and 950 $cm^{-1}$, showing two separate peaks with wave numbers of 810 $cm^{-1}$ and 880 $cm^{-1}$.
FIG. 6 illustrates how the ratio between the areas of the two peaks at 810 $cm^{-1}$ and 880 $cm^{-1}$ in the FT-IR spectrum in FIGS. 4 and 5 is related to the degradation of power characteristics of a high-output FET.

FIG. 4 shows an FT-IR spectrum obtained from a silicon oxide film deposited on a gallium-arsenide (GaAs) wafer substrate by low-pressure chemical vapor deposition (CVD). Peaks appear at wave numbers of 810 $cm^{-1}$, 880 $cm^{-1}$, 1060 $cm^{-1}$, and 1160 $cm^{-1}$, the latter two of these peaks being superimposed in a way that makes them appear to be a single peak. FIG. 5 shows an enlargement of the FT-IR spectrum in FIG. 4 between wave numbers 700 $cm^{-1}$ and 950 $cm^{-1}$, showing how this part of the spectrum can be analyzed as a sum of two separate peaks at 810 $cm^{-1}$ and 880 $cm^{-1}$.

The FT-IR data shown in FIGS. 4 and 5 were obtained by using FT-IR transmission spectroscopy to analyze a silicon oxide film deposited on a dummy GaAs wafer substrate simultaneously with the deposition of a silicon oxide film 5 by low-pressure CVD during the fabrication of the high-output FET shown in FIG. 1. It is also possible to use attenuated total reflection (ATR) spectroscopy or reflectance anisotropy spectroscopy (RAS), or to use a micro-infrared spectroscopy technique capable of measuring reflectance.

FIG. 6 indicates how the ratio between the areas of the two peaks at wave numbers of 810 $cm^{-1}$ and 880 $cm^{-1}$ in the FT-IR spectrum is related to the degradation of power characteristics of a high-output FET. Samples 1, 2, and 3 are three high-output FETs. Each sample has the sectional structure shown in FIG. 1. Only the qualities of the silicon oxide interlayer films of these samples differ, because the fabrication process conditions were the same except for the process conditions for the interlayer films. Each sample had a gate length of 0.8 µm, a gate width of 3.5 µm, and a unit gate width of 175 µm.

In FIG. 6, the silicon oxide film area ratio is the value obtained by dividing the area of the peak at wave number 810 $cm^{-1}$ by the area of the peak at wave number 880 $cm^{-1}$ in the FT-IR spectrum of the silicon oxide film. Po indicates the value of the starting power, expressed in decibels (dB), of a high-output FET before an extended drive test. ΔP indicates the value obtained by subtracting the value of the starting power Po from the value of the power of the high-output FET at the end of the drive test (lasting 48 hours). The negative value indicated by ΔP indicates degradation of the power characteristic.

The procedure by which the data in FIG. 6 were obtained will be described below. Fabrication process conditions were set and samples 1, 2, and 3 were fabricated, yielding silicon oxide film area ratios of 0.099 for sample 1, 0.141 for sample 2, and 0.183 for sample 3, as obtained from FT-IR spectra. The silicon oxide films were formed on a GaAs wafer substrate by low-pressure CVD.

The interlayer film fabrication process conditions that affect the silicon oxide film area ratio include the flow rates of silane ($SiH_4$) and oxygen gases (including flow rates of their carrier gases), the film fabrication temperature and pressure, and under certain circumstances, the thickness of the silicon oxide film.

On each of the samples fabricated as described above, the initial power Po before the start of the 48-hour drive test was measured, the power after 48 hours of driving was measured, and the degradation ΔP of the power characteristic due to the extended operation of the FET was obtained.

As shown in FIG. 6, as the silicon oxide film area ratio (the area ratio at wave numbers of 810 $cm^{-1}$ and 880 $cm^{-1}$ in an FT-IR spectrum) decreased, so did the degradation of the power characteristic of the high-output FET.

This indicates that the degradation of power characteristics of a high-output FET having a silicon oxide film, during operation of the FET, can be controlled during the fabrication of the silicon oxide interlayer film, by determining fabrication process conditions for the silicon oxide film from the silicon oxide film area ratio at wave numbers of 810 $cm^{-1}$ and 880 $cm^{-1}$ in the FT-IR spectrum. More specifically, the degradation of power characteristics of a high-output FET can be mitigated by fabricating the silicon oxide film under process conditions that reduce the area ratio.

It was confirmed that after the degradation caused by 48 hours of operation, the power of samples 1, 2, and 3 returned to the initial level Po if each sample was held at a temperature of 120° C. for 24 hours. This indicates the occurrence of a reversible reaction in the high-output FET samples: their power characteristics degrade during operation, but after operation stops, the degradation will disappear if the samples are stored for an extended period of time. The reason is thought to be that the degradation is not due to chemical structural changes in the FET materials, but to electron trapping.

Figure 7:
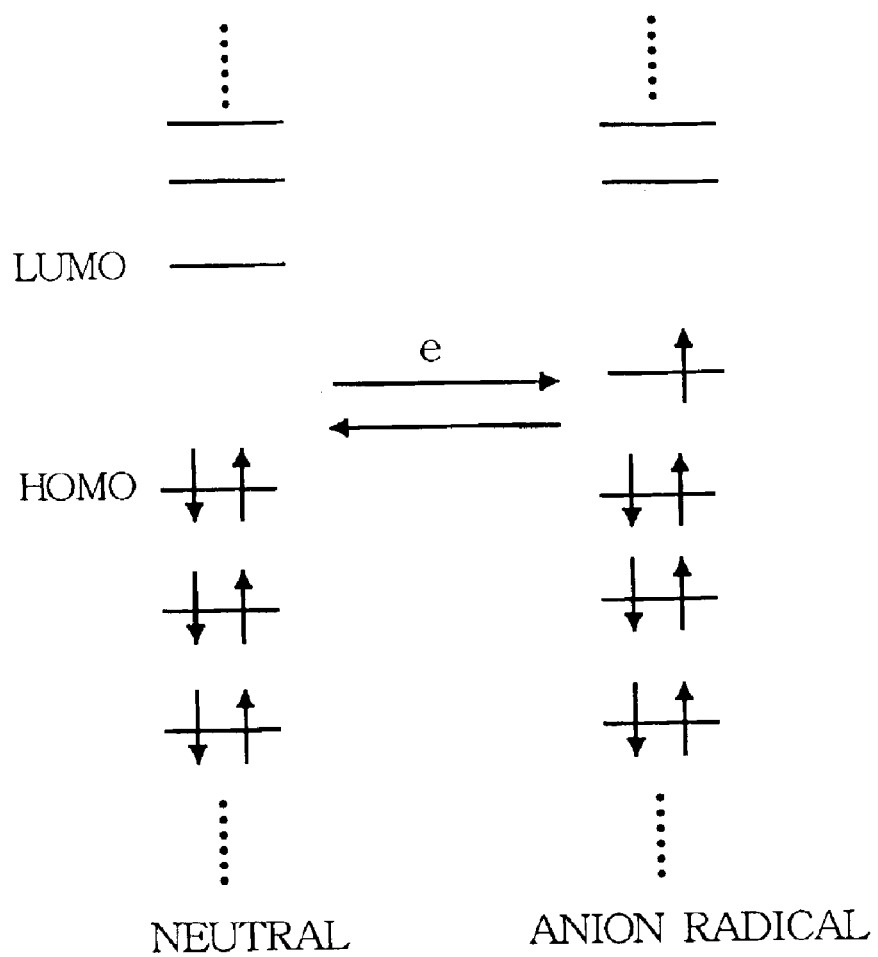
FIG. 7 schematically illustrates the state of electrons trapped in a silicon oxide film.

FIG. 7 schematically illustrates the state of electrons trapped in a silicon oxide film. When a single electron enters a neutral state, the neutral state changes into an anion radical state. If no chemical structural change occurs in the anion radical state, then the reaction is reversible.

The silicon oxide film trapping the electrons is thought to have an amorphous structure formed not only by silicon-oxygen-silicon (Si—O—Si) bonds but also by silicon-silicon (Si—Si) bonds.

A molecular orbital calculation was performed to show that in a silicon oxide film including Si—Si bonds, the Si—Si bonds operate as electron traps. The PC Spartan Pro Program version 1.0.5 (Wavefunction Inc.) was used to calculate an optimum structure by the parameterized model 3 (PM3) method.

Figure 8:
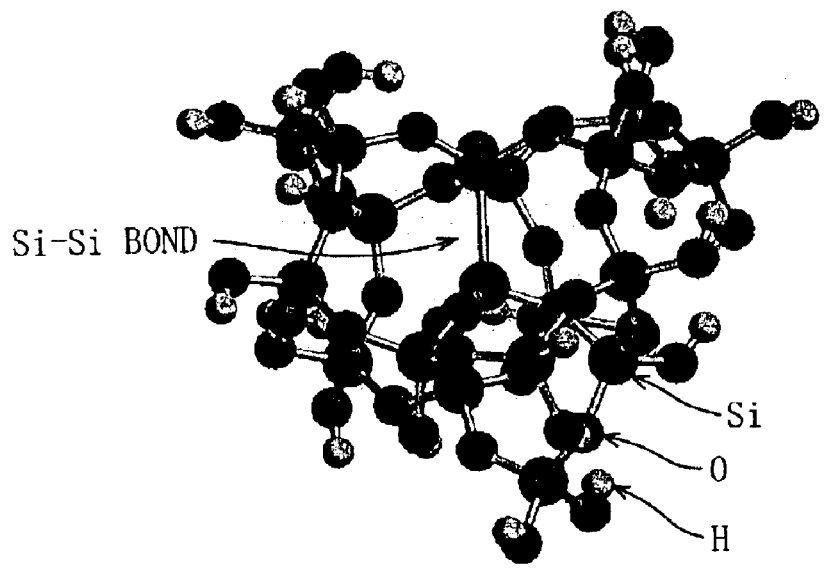
FIG. 8 is a perspective view of the structure of a model of a silicon oxide film having Si—Si bonds.

FIG. 8 is a perspective view of the structure of a model of a silicon oxide film having Si—Si bonds used for the molecular orbital calculation. Since an enormous amount of time would be required to calculate an amorphous structure directly, the model had Si—O—Si bonds placed appropriately around Si—Si bonds, and was terminated by hydrogen atoms.

Figure 9:
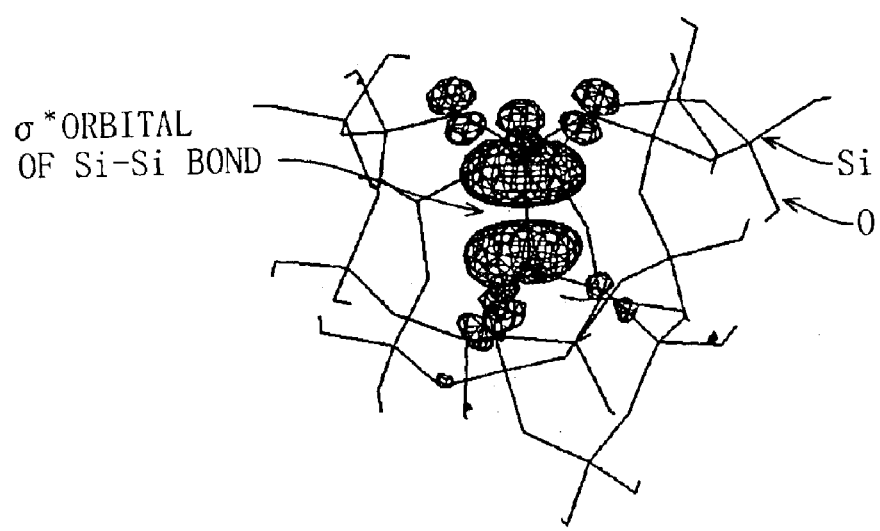
FIG. 9 shows the lowest unoccupied molecular orbital (LUMO) of the structure in FIG. 8.

FIG. 9 shows the lowest unoccupied molecular orbital (LUMO) of the structure in FIG. 8 obtained by the molecular orbital calculation. The LUMO is spread over the Si—Si bonds. More specifically, the σ* orbital of the Si—Si bonds becomes the LUMO. This indicates the possibility that the Si—Si bonds may operate as electron traps in the silicon oxide film.

In the FT-IR spectrum of the silicon oxide film, Si—O stretching vibration is indicated by the peak at wave number 810 cm$^{-1}$, and Si—Si stretching vibration is indicated by the peak at wave number 880 cm$^{-1}$. The area ratio at the two peaks in the FT-IR spectrum is used as an index of the quantity of Si—Si bonds in the silicon oxide film.

The critical area is the area of peak at the wave number of 880 cm$^{-1}$, where Si—Si stretching vibration is indicated. The area of the peak at the wave number of 810 cm$^{-1}$, where Si—O stretching vibration is indicated, can be replaced by the area of a peak at another wave number indicating Si—O stretching vibration, such as the peak at wave number 1060 cm$^{-1}$ or 1160 cm$^{-1}$. In the embodiment described above, the area ratio was determined by using the peak at wave number 810 cm$^{-1}$ because of easy peak identification. It is also possible to use the area of the peak at wave number 880 cm$^{-1}$ as an index of the quantity of Si—Si bonds in the silicon oxide film.

The activation energy when a silicon oxide film having Si—Si bonds operates as an electron trap was determined from a molecular orbital calculation. The PC Spartan Pro Program version 1.0.5 (Wavefunction Inc.) was used to calculate an optimum structure by the PM3 method for the structure in FIG. 8. The gross energy at the transition state, that is, the difference between the gross energy in the neutral state and the gross energy in the anion radical state, was calculated and the gross energy difference was determined as the activation energy.

Figures 10, 11:
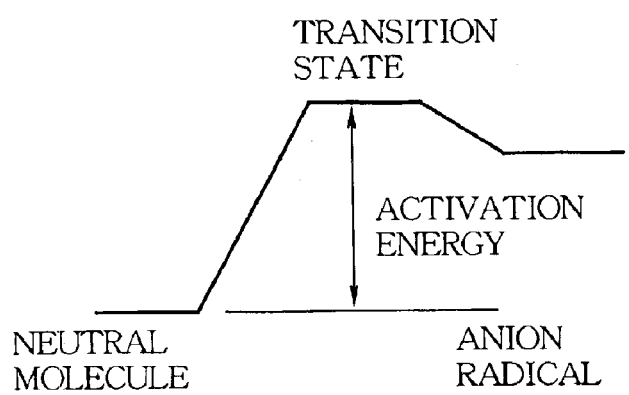
FIG. 10 is a graph illustrating the activation energy when a silicon oxide film operates as an electron trap.
FIG. 11 is a table of activation energy values when a silicon oxide film operates as an electron trap.

FIG. 10 is a graph illustrating the activation energy determined by the calculation above when a silicon oxide film operates as an electron trap. FIG. 11 illustrates the activation energy by comparing the activation energy when a silicon oxide film having Si—Si bonds operates as an electron trap with the activation energy when a silicon oxide film having silicon-hydrogen (Si—H) bonds operates as an electron trap.

The value of the activation energy when a silicon oxide film has Si—Si bonds is approximately 5.88 kcal/mol. This value is approximately half the value of the activation energy when a silicon oxide film has Si—H bonds, as indicated in FIG. 11. This indicates the validity of the theory that Si—Si bonds operate as electron traps.

When an anion radical state reverts to a neutral state, if the silicon oxide film has Si—Si bonds, the value of the activation energy obtained by calculations similar to the calculations giving the values in FIG. 11 is approximately 1.66 kcal/mol. This indicates that the anion radical state reverts to the neutral state in a reversible reaction with very little structural change.

As described above, it can be considered that Si—Si bonds operating as electron traps in a silicon oxide film cause the degradation of power characteristics of a high-output compound semiconductor FET having a silicon oxide film, due to operation of the FET.

Accordingly, if the quantity of Si—Si bonds in the silicon oxide film is controlled, the power degradation of the high-output FET can be controlled. More specifically, if the quantity of Si—Si bonds in the silicon oxide film is reduced, the power degradation of the high-output FET can be reduced. It is possible to control the quantity of Si—Si bonds in the silicon oxide film on the basis of the peak at wave number of 810 cm$^{-1}$ in the FT-IR spectrum of the silicon oxide film (by measuring the area the area of the peak at wave number of 810 cm$^{-1}$, or by measuring the ratio of the area of this peak to the area of a peak at another wave number).

Three examples of silicon oxide interlayer film fabrication processes embodying the present invention are described below.

EXAMPLE 1

A silicon oxide film deposited on a dummy GaAs wafer substrate is analyzed by using FT-IR spectroscopy. From the peak at wave number 810 cm$^{-1}$ in the FT-IR spectrum, fabrication process conditions for forming the silicon oxide film are determined so as to reduce the quantity of Si—Si bonds, which is used as an index of the expected FET power characteristic degradation. A silicon oxide interlayer film is formed according to these fabrication process conditions on a GaAs wafer substrate product used for the fabrication of a high-output FET.

EXAMPLE 2

The silicon oxide interlayer film is formed on a GaAs wafer substrate product used for the fabrication of a high-output FET. This silicon oxide interlayer film is analyzed by using, for example, a micro-infrared spectroscopy technique capable of measuring reflectance. From the peak at wave number 810 cm$^{-1}$ in the FT-IR spectrum, the quantity of Si—Si bonds is estimated as an index of expected FET power characteristic degradation. The quality of the interlayer film is determined from the estimated quantity of Si—Si bonds.

EXAMPLE 3

The fabrication process conditions are determined by using FT-IR spectroscopy as described in Example 1, and the interlayer film is evaluated as described in Example 2.

As described above, the present invention enables the degradation of power characteristics of a FET to be evaluated and controlled by a simple method during the silicon oxide interlayer film fabrication process. A drive test over an extended period of time is not required, so degradation can be evaluated quickly.

The embodiment described above has dealt with a high-output FET on a GaAs substrate having a silicon oxide film, but the invention can also be applied to a high-output FET on another compound substrate, such as an indium-phosphorus substrate or a gallium-nitride substrate, having a silicon oxide interlayer film.

As described above, the invention has the effect of evaluating and controlling the degradation of power characteristics of an FET simply and quickly during the silicon oxide interlayer film fabrication process.

Those skilled in the art will recognize that further variations are possible within the scope of the invention, which is defined in the appended claims.

What is claimed is:

1. A method of fabricating a semiconductor device including a field-effect transistor (FET) having a silicon oxide interlayer film formed on a compound semiconductor substrate, the method comprising:

forming a silicon oxide film on a first compound semiconductor substrate;

analyzing the silicon oxide film by FT-IR spectroscopy to obtain an FT-IR spectrum;

estimating a quantity of silicon-silicon bonds operating as electron traps from a peak with a wave number of 880 cm$^{-1}$ in the FT-IR spectrum, indicating silicon-silicon stretching vibration;

determining a fabrication process condition for forming the silicon oxide interlayer film so as to reduce the quantity of silicon-silicon bonds therein;

forming the silicon oxide interlayer film on a second compound semiconductor substrate according to the determined fabrication process condition; and forming the FET on the second compound semiconductor substrate, incorporating the silicon oxide interlayer film.

2. The method of claim 1, wherein the quantity of the silicon-silicon bonds is estimated from an area of said peak.

3. The method of claim 2, wherein estimating the quantity of silicon-silicon bonds comprises comparing an area of said peak with an area of another peak, having a different wave number, indicating silicon-oxygen stretching vibration.

4. The method of claim 3, wherein said another peak has a wave number of 810 $cm^{-1}$.

5. The method of claim 2, wherein said fabrication process condition is a gas flow rate.

6. The method of claim 2, wherein said fabrication process condition is a gas film fabrication temperature.

7. The method of claim 2, wherein said fabrication process condition is a gas film fabrication pressure.

8. The method of claim 2, wherein said fabrication process condition is a thickness of the silicon oxide interlayer film.

9. A method of fabricating a semiconductor device, including a FET having a silicon oxide interlayer film formed on a compound semiconductor substrate, the method comprising:

forming the silicon oxide interlayer film on the compound semiconductor substrate;

analyzing the silicon oxide interlayer film by FT-IR spectroscopy to obtain an FT-IR spectrum;

estimating a quantity of silicon-silicon bonds operating as electron traps in the silicon oxide interlayer film from a peak with a wave number of 880 $cm^{-1}$ in the FT-IR characteristic, indicating silicon-silicon stretching vibration; and using the estimated quantity as an index of expected power performance degradation during operation of the FET.

10. The method of claim 9, wherein the quantity of the silicon-silicon bonds is estimated from the area of said peak.

11. The method of claim 10, wherein estimating the quantity of silicon-silicon bonds comprises comparing an area of said peak with an area of another peak, having a different wave number, indicating silicon-oxygen stretching vibration.

* * * * *